United States Patent [19]

Fukushima et al.

[11] Patent Number: 5,233,068

[45] Date of Patent: Aug. 3, 1993

[54] ORGANIC SILICON COMPOUNDS AND METHOD FOR MAKING

[75] Inventors: Motoo Fukushima; Shigeru Mori, both of Kawasaki, Japan

[73] Assignee: Shin-Etsu Chemical Co., Ltd., Tokyo, Japan

[21] Appl. No.: 978,543

[22] Filed: Nov. 19, 1992

[30] Foreign Application Priority Data

Nov. 20, 1991 [JP] Japan ................ 3-331441

[51] Int. Cl.$^5$ ................................. C07F 7/08
[52] U.S. Cl. ................................... 556/430
[58] Field of Search ........................ 556/430

[56] References Cited

U.S. PATENT DOCUMENTS 3,165,494  1/1965  Smith ..................... 556/430 X
4,626,583 12/1985  Arkles .................... 556/430 X
4,962,174 10/1990  Bilgrieu et al. ........... 556/430 X

OTHER PUBLICATIONS

Wu et al., (1973), Journal of Chem. Eng. Data, vol. 18, No. 3, pp. 350-352.
Carlson et al. (1983), Organometallics, vol. 2, No. 12, pp. 1801-1807.
Ishikawa et al. (1983), Polymer Letters Ed., vol. 21, pp. 657, 660.
Soysa et al. (1977), J. Organometal. Chem., vol. 133, No. 2, pp. C17-C20.

Primary Examiner—Paul F. Shaver
Attorney, Agent, or Firm—Millen, White, Zelano & Branigan

[57] ABSTRACT

Novel cyclic organic silicon compounds of formula (1) can be synthesized in high yields and high purity by reacting a dichlorosilane of formula (3) with a cyclotrisiloxane of formula (4) in an aprotic polar solvent to form an α,ω-dichlorosiloxane of formula (2), and reacting the α,ω-dichlorosiloxane with an alkali metal according to the following reaction scheme.

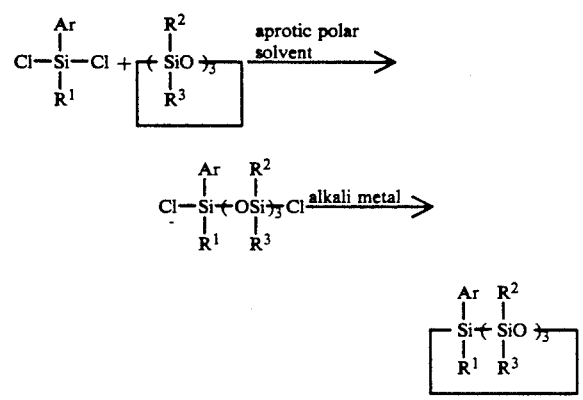

3 Claims, 6 Drawing Sheets

ORGANIC SILICON COMPOUNDS AND METHOD FOR MAKING

BACKGROUND OF THE INVENTION

1. Field of the Invention

This invention relates to novel cyclic organic silicon compounds having a Si—Si bond to which an aryl group such as a phenyl, tolyl or naphthyl group is attached and a method for preparing the same.

2. Prior Art

For the purpose of using siloxanes as resists, several attempts were made in the prior art to increase the reactivity of siloxanes by incorporating a Si—Si bond therein as reported by Ishikawa, Journal of Polymer Science, 21, p657 (1983). It was difficult to incorporate a controlled amount of Si—Si bond into siloxanes having an increased number of recurring Si—O—Si linkages.

In the silicone industry, it is practiced to produce high molecular weight polysiloxanes through ring-opening polymerization of cyclic siloxanes such as octamethylcyclotetrasiloxane in the presence of an acid or alkali catalyst. If a method capable of producing a siloxane having a Si—Si bond in high yields and high purity is available, then it is possible to incorporate a controlled amount of Si—Si bond into polysiloxanes. However, the prior art methods failed to produce a siloxane having a Si—Si bond in a practically acceptable manner.

Known synthetic methods of siloxanes having a Si—Si bond are by condensation of silanols with chlorosilanes as reported by Wu, Journal Chemical Engineering Data, 18 (3), p350 (1973), by oxidation of polysilanes as reported by West, Organometallics, 1 (12), p1801 (1983), and by introducing silylene into siloxanes as reported by Weber, Journal of Organometallic Chemistry, 133 (2), C17 (1977). These methods are not commercially feasible because of restricted supply of starting reactants and low product yields.

SUMMARY OF THE INVENTION

Therefore, an object of the present invention is to provide a novel organic silicon compound or cycle siloxane having a Si—Si bond to which an aryl group is attached.

Another object of the present invention is to provide a method for preparing such an organic silicon compound in high yields and high purity.

We have found that a cyclic organic silicon compound of formula (1) can be synthesized in high yields and high purity by reacting an α,ω-dichlorosiloxane of formula (2) with an alkali metal, which α,ω-dichlorosiloxane is, in turn, obtained as by reacting a dichlorosilane of formula (3) with a cyclotrisiloxane of formula (4) in an aprotic polar solvent. The reaction scheme is shown below.

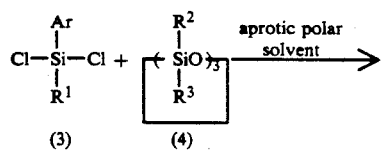

(3) (4)

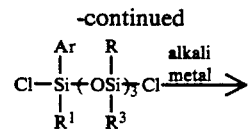

(2)

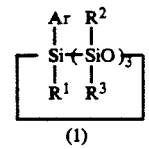

(1)

In the formulae, Ar is a substituted or unsubstituted aryl group having 6 to 14 carbon atoms, $R^1$, $R^2$ and $R^3$ are independently monovalent hydrocarbon groups having 1 to 6 carbon atoms.

The thus synthesized organic silicon compound of formula (1) has a great ultraviolet radiation absorption band in the wavelength (γ) range of 260 to 230 nm and is thus useful as a photo-reactive functional group. By copolymerizing this organic silicon compound with a cyclic siloxane, a controlled amount of Si—Si bond can be introduced into the polysiloxane to form a photo-reactive material which is useful as a photo-resist. Further, since the Si—Si bond of the organic silicon compound is susceptible to reaction, novel cyclic siloxanes can be synthesized from the organic silicon compound by reacting it with ArC≡CH in the presence of a catalyst such as a palladium complex in accordance with the reaction scheme shown below.

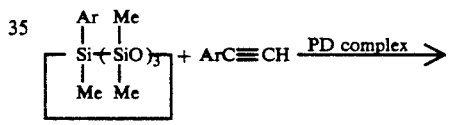

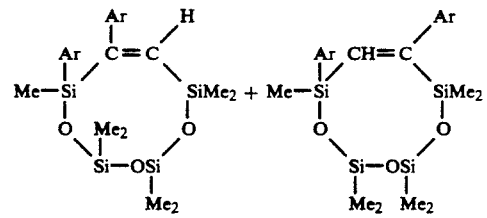

In the formulae, Me is methyl and Ar is as defined above.

Therefore, the present invention provides organic silicon compounds of formula (1) and a method for preparing them by reacting an α,ω-dichlorosiloxane of formula (2) with an alkali metal.

DETAILED DESCRIPTION OF THE INVENTION

Figure 1:
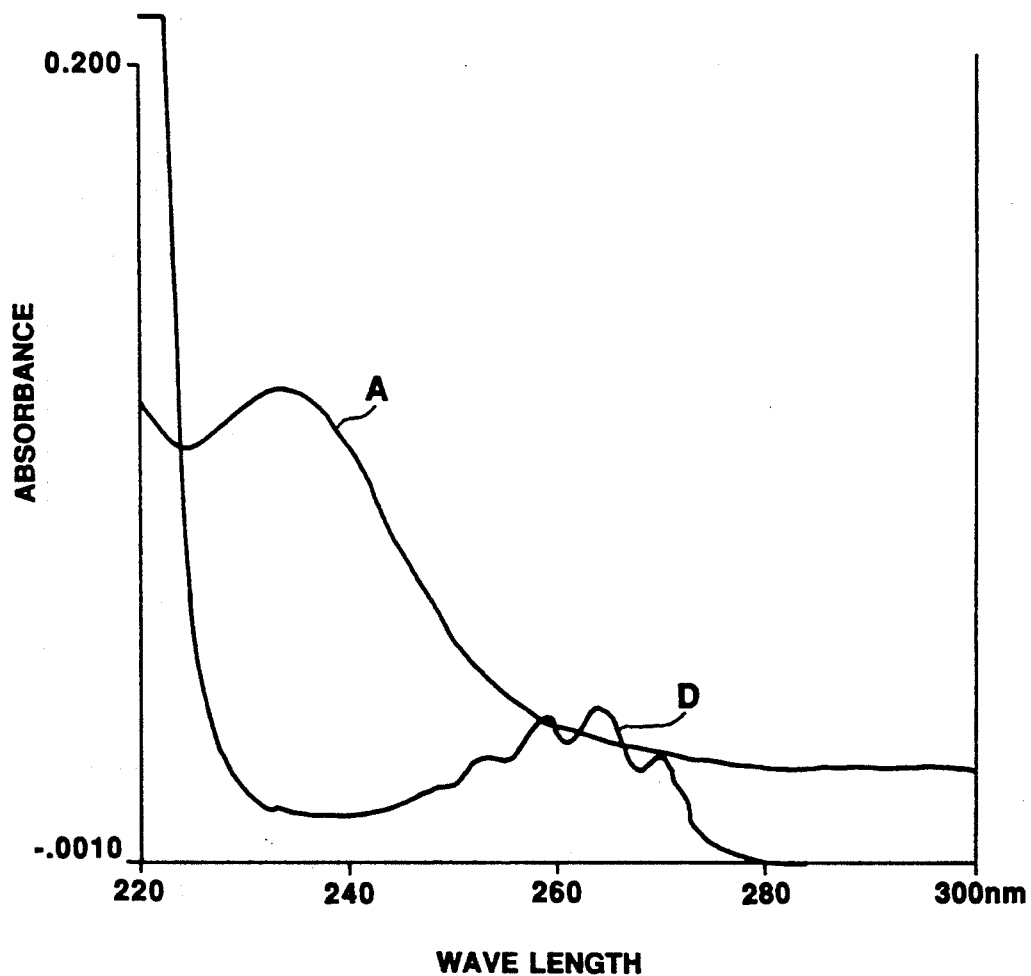
FIG. 1 is a UV absorption spectrum chart of the organic silicon compounds of Example 1 and Comparative Example 2.

The organic silicon compounds of the present invention are of the general formula (1).

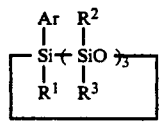
(1)

In formula (1), Ar is a substituted or unsubstituted aryl group having 6 to 14 carbon atoms, for example, phenyl, tolyl and naphthyl groups, with the phenyl group being preferred; and $R^1$, $R^2$ and $R^3$, which may be identical or different, are monovalent hydrocarbon groups having 1 to 6 carbon atoms, for example, alkyl groups such as methyl, ethyl and propyl groups and phenyl and other groups.

Illustrative examples of the organic silicon compound are given below.

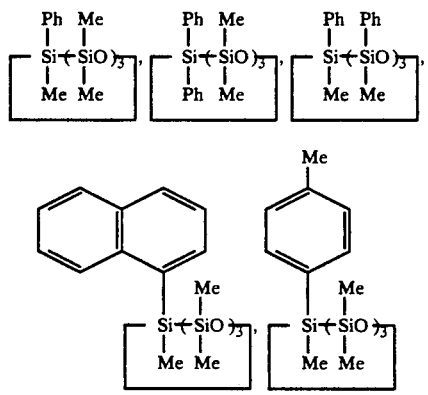

In the formulae, Me is methyl and Ph is phenyl.

The compounds of formula (1) can be synthesized through dechlorination reaction of an α,ω-dichlorosiloxane of formula (2) with an alkali metal.

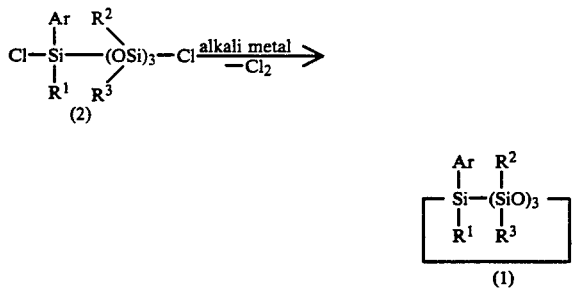

Preferably, the alkali metal is sodium or lithium and used in an amount of about 2 to 2.5 mol per mol of the compound of formula (2). Where sodium is used, synthesis may be done in the presence of a non-polar solvent such as toluene, xylene and dodecane at a temperature of 80° to 180° C., preferably at the reflux temperature of the solvent over 1 to 8 hours. Where lithium is used, synthesis may be done in the presence of a polar solvent such as tetrahydrofuran and diethyl ether at a temperature of −75° to 40° C., preferably at nearly room temperature over 1 to 8 hours. In either case, reaction is preferably effected in an inert gas such as nitrogen gas.

The α,ω-dichlorosiloxane of formula (2) is, in turn, readily obtained by reacting a dichlorosilane of formula (3) with a cyclotrisiloxane of formula (4) in a proton-free polar solvent in accordance with the following reaction scheme. In this reaction, each of the dichlorosilane of formula (3) and the cyclotrisiloxane of formula (4) may be used as a single compound or a mixture of two or more.

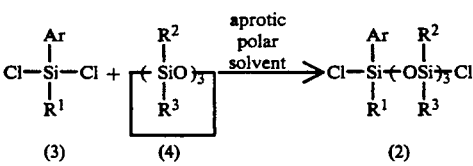

Preferably, the dichlorosilane of formula (3) and the cyclotrisiloxane of formula (4) are used in equimolar amounts. Preferred reaction conditions include 0° to 50° C. and 1/10 to 3 hours, more preferably 25° C. and ½ hour. Reaction temperature above 50° C. and undesirable because equilibration reaction at such higher temperatures results in dichlorosiloxanes having three silicon atoms and five or more silicon atoms in addition to the dichlorosiloxane having four silicon atoms.

Examples of the aprotic polar solvent which is used as a catalyst in the reaction include hexamethylphosphoric triamide (HMPA), dimethylsulfoxide (DMSO) and dimethylformamide (DMF). The solvent is preferably added in amounts of about 0.01 to 10% by weight, more preferably about 0.1 to 2% by weight based on the total weight of the dichlorosilane of formula (3) and the cyclotrisiloxane of formula (4). With less than 0.01% by weight of the solvent, reaction takes a long time until completion. With more than 10% by weight of the solvent, the product would be obtained in admixture with the solvent and thus difficult to separate therefrom.

The thus synthesized organic silicon compound of formula (1) has a great ultraviolet radiation absorption band in the wavelength (λ) range of 260 to 230 nm and is thus useful as a photo-reactive functional group. By copolymerizing this organic silicon compound with a cyclic siloxane, a controlled amount of Si—Si bond can be introduced into the polysiloxane to form a photo-reactive material which is useful as a photo-resist.

Moreover, by using the organic silicon compound of formula (1) as a starting reactant, that is, by reacting it with an acetylene compound in the presence of a palladium complex catalyst, a cyclic siloxane having an Ar group (Ar is as defined above) and a carbon-to-carbon double bond can be synthesized. This cyclic siloxane, in turn as a monomer can be copolymerized with another conventional cyclic siloxane, thereby introducing into the polysiloxane compound a —Si—O—Si— linkage having a carbon-to-carbon double bond available for crosslinking.

EXAMPLE

Examples of the invention are given below by way of illustration and not by way of limitation. All percents are by weight. Me is methyl and Ph is phenyl.

EXAMPLE 1

A 50-ml flask was charged with 11.1 grams (50 mmol) of hexamethylcyclotrisiloxane and 9.5 grams (50 mmol) of phenylmethyldichlorosilane, to which 0.2 grams (1%) of HMPA was added as a catalyst. The mixture was stirred for ½ hour at room temperature. The reaction mixture was transferred to a distillation pot and a fraction at 100°-104° C. under a vacuum of 2 mmHg was collected. There was obtained 18.8 grams (yield 91%) of an α,ω-dichlorosiloxane of formula (6). The reaction scheme is shown below.

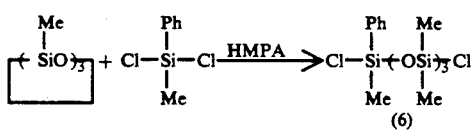

(6)

Next, a 100-ml three-necked flask was charged with 20 ml of xylene and 0.48 grams (21 mmol) of metallic sodium and nitrogen gas was passed. With stirring and heating under reflux, 4.13 grams (10 mmol) of the α,ω-dichlorosiloxane of formula (6) was added dropwise to the flask. As the siloxane was added, exothermic reaction took place and the metallic sodium was consumed. After refluxing for 3 hours, the reaction mixture was combined first with 1 ml of water and then with 50 ml of toluene and 100 ml of water for washing purposes. After water washing, the organic layer was separated and dried over magnesium sulfate. The salt was removed by filtration, the toluene and xylene were removed by vacuum distillation, and finally a fraction at 80°-120° C. under 2 mmHg was collected. There was obtained 2.6 grams (yield 75%) of a cyclic siloxane having a Ph—Si—Si linkage represented by formula (7). The distillation residue was 0.68 grams (yield 20%) of a polymer represented by formula (8).

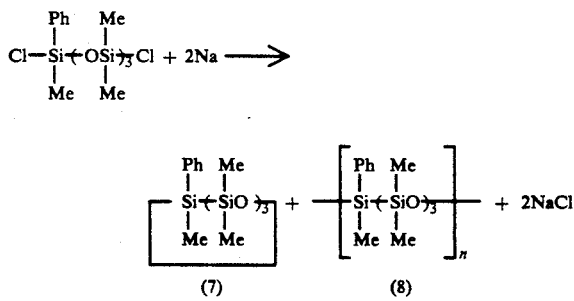

Figure 2:
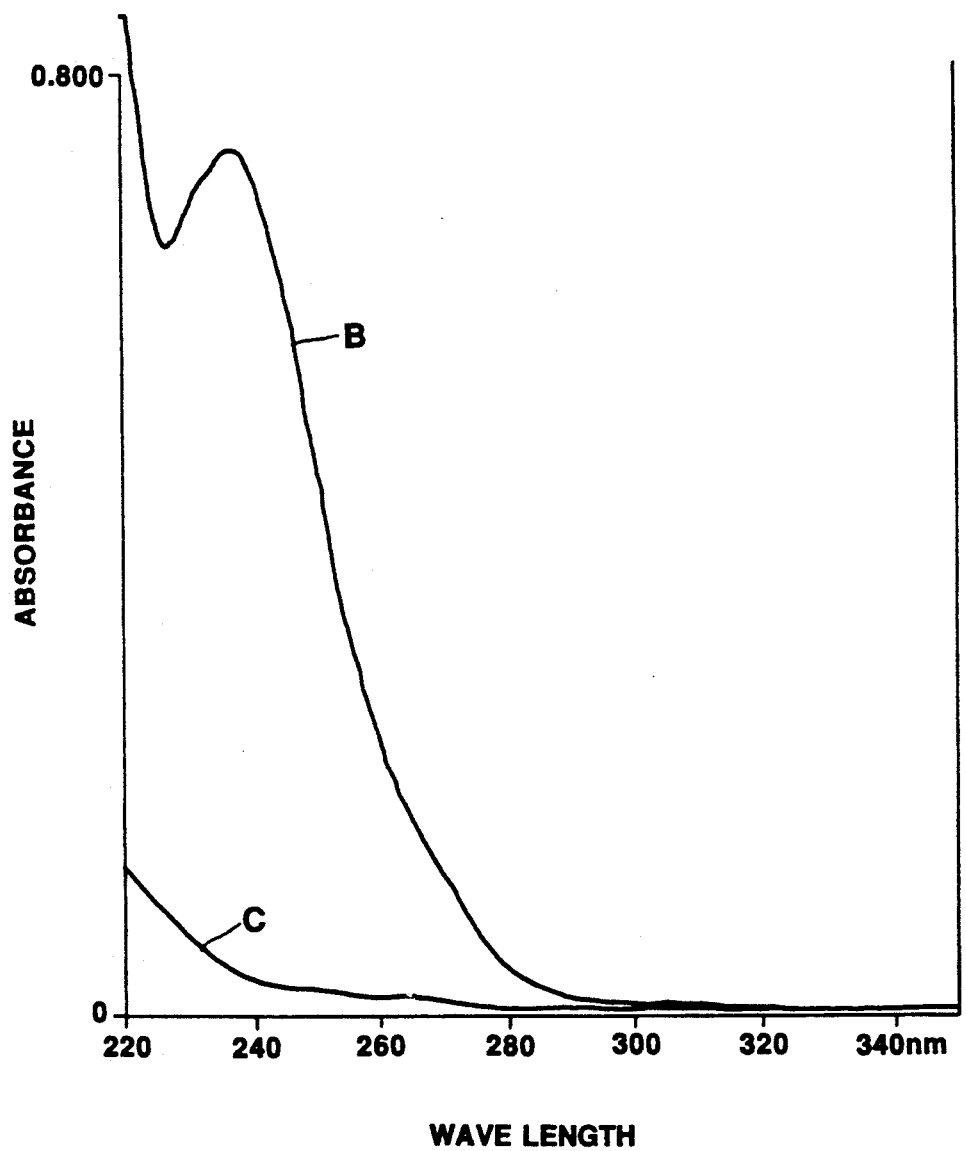
FIG. 2 is a UV absorption spectrum chart of the siloxane polymers of Example 1 and Comparative Example 1.
Figure 3:
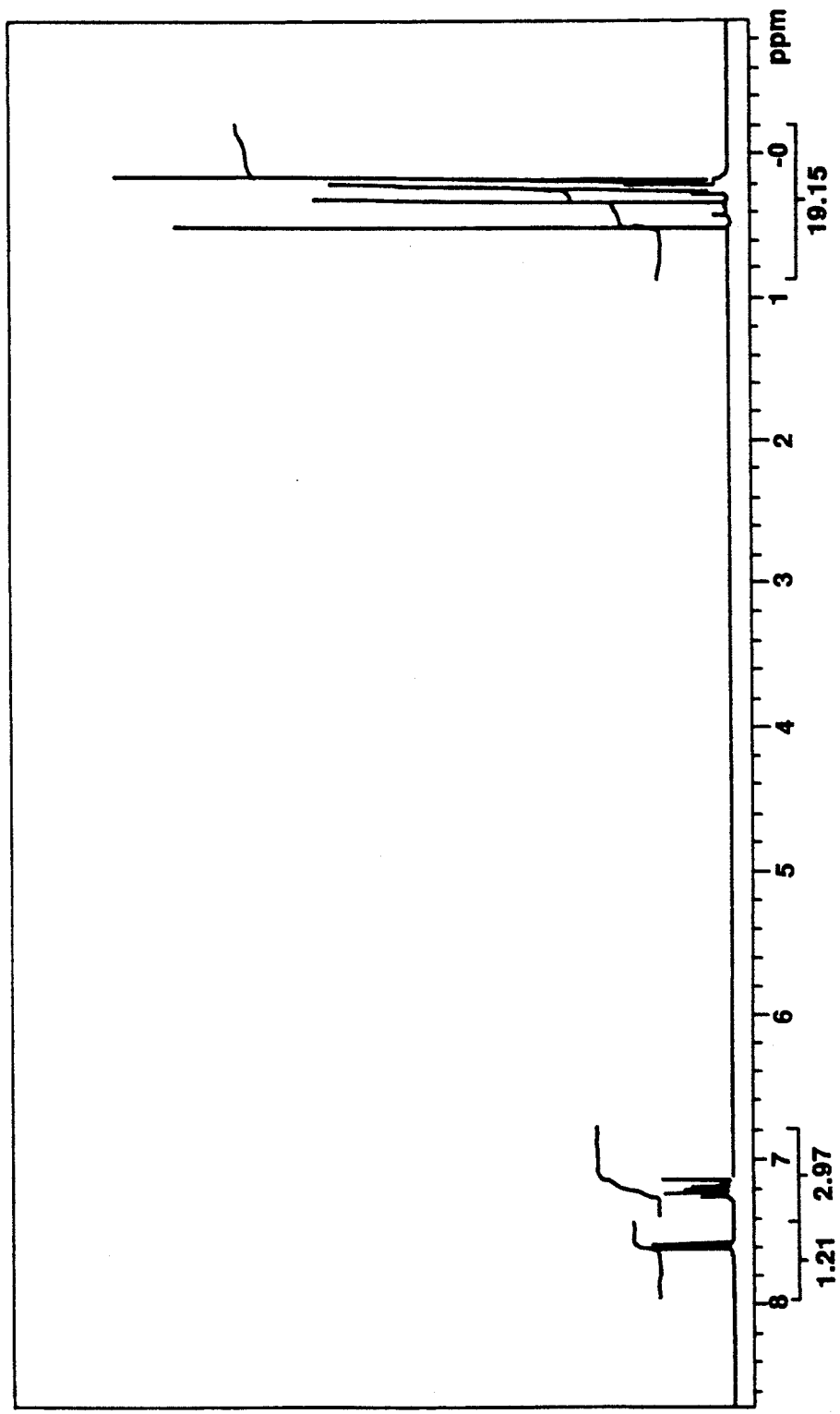
FIG. 3 is a NMR spectrum chart of the organic silicon compound of Example 1.
Figure 4:
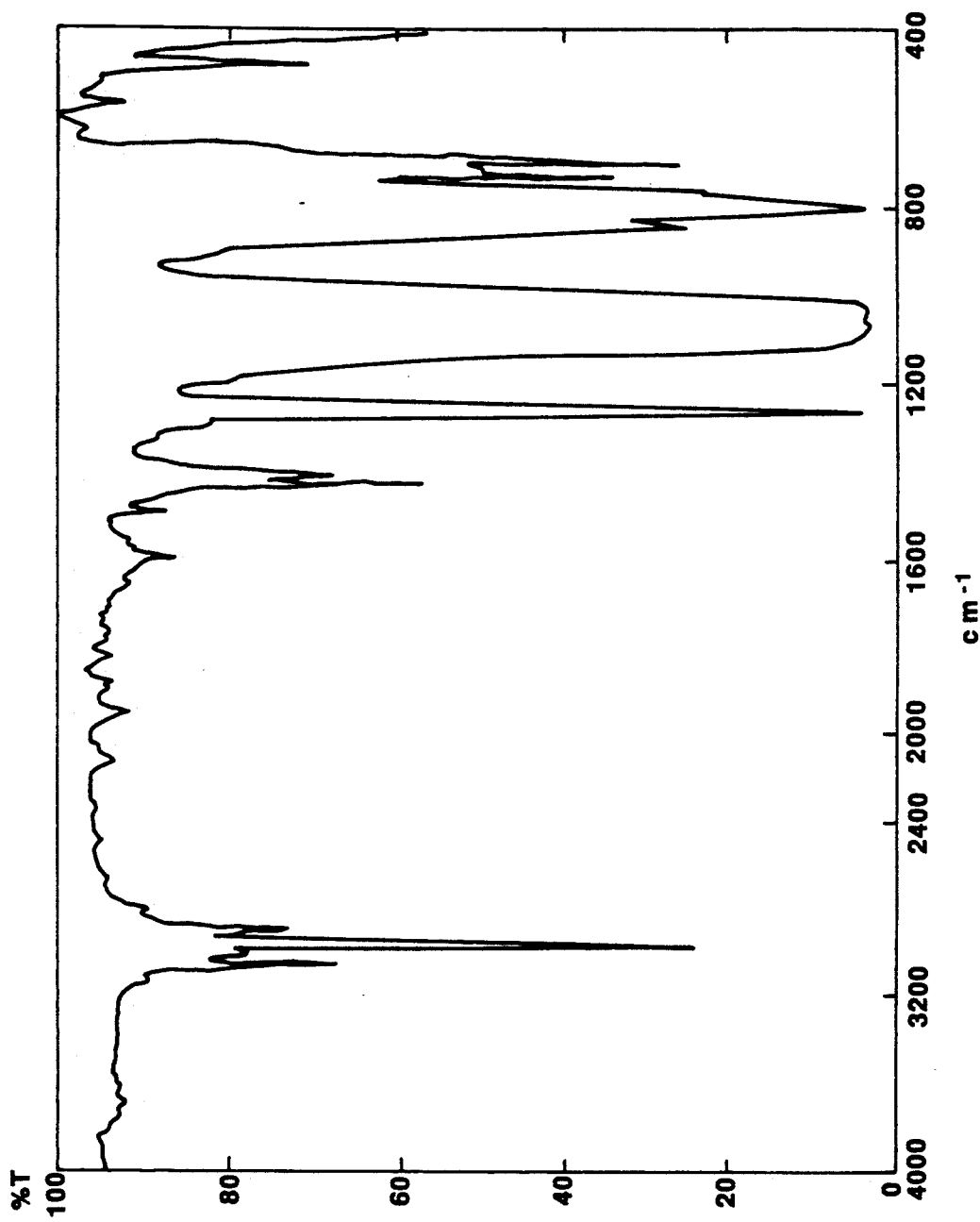
FIG. 4 is a IR spectrum chart of the organic silicon compound of Example 1.

The cyclic siloxane of formula (7) was analyzed by spectroscopy, with its UV spectrum shown in FIG. 1 as curve A, NMR spectrum shown in FIG. 3, and IR spectrum shown in FIG. 4. The UV spectrum of the polymer of formula (8) is shown in FIG. 2 as curve B.

Comparative Example 1

The initial step of Example 1 was repeated except that 6.4 grams of dimethyldichlorosilane was used instead of the phenylmethylchlorosilane. An α,ω-dichlorosiloxane was obtained in accordance with the following reaction scheme.

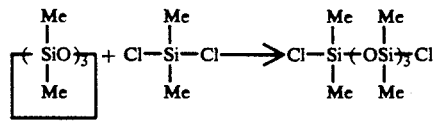

Next, as in Example 1, the thus obtained α,ω-dichlorosiloxane was added dropwise to a mixture of xylene and metallic sodium. No exothermic reaction took place. The reaction mixture was heated under reflux for 3 hours. It was found that only part of the sodium was consume. Gas chromatographic analysis of the reaction mixture revealed that some α,ω-dichlorosiloxane was left unreacted and a cyclic siloxane having a Si—Si bond was little formed.

The sodium was removed from the reaction mixture by filtration, and the α,ω-dichlorosiloxane was then removed by vacuum distillation. The residual xylene solution was washed with water, dried over magnesium sulfate, and then stripped, obtaining 0.72 grams (yield 25%) of a siloxane polymer having a Si—Si bond, but free of a phenyl group. The reaction scheme is shown below. The UV spectrum of this siloxane polymer is shown in FIG. 2 was curve C.

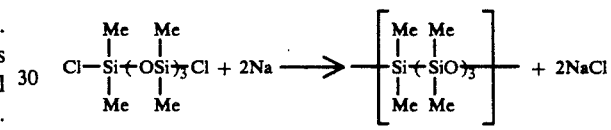

Comparative Example 2

In 15 ml of diethyl ether was dissolved 5 grams of the α,ω-dichlorosiloxane of formula (6) obtained in Example 1. The mixture was added to water for hydrolysis. The ether layer was washed with water, dried, and then vacuum distilled, obtaining a cyclic siloxane having a Ph—Si bond, but free of a Si—Si bond. The reaction scheme is shown below. The UV spectrum of this cyclic siloxane is shown in FIG. 1 as curve D.

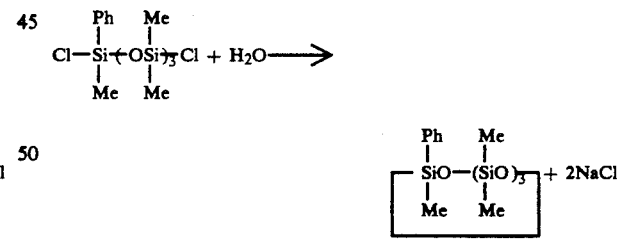

The following Reference Example is to illustrate the synthesis of a novel cyclic siloxane from a cyclic siloxane according to the present invention.

REFERENCE EXAMPLE

A flask was charged with 0.34 grams (1 mmol) of the cyclic siloxane of formula (7) in Example 1 and 0.302 grams (2 mmol) of phenylacetylene, purged with argon, then charged with 2.6 mg (0.01 mmol) of $PdCh_2(CH_3CN)_2$ and 3.2 mg (0.02 mmol) of $P(OCH_2)_3CC_2H_5$, purged again with argon, and thereafter, heated for reaction at 120° C. for 1.5 hours in a nitrogen stream. Gas chromatography showed that all the cyclic siloxane was consumed.

Figure 5:
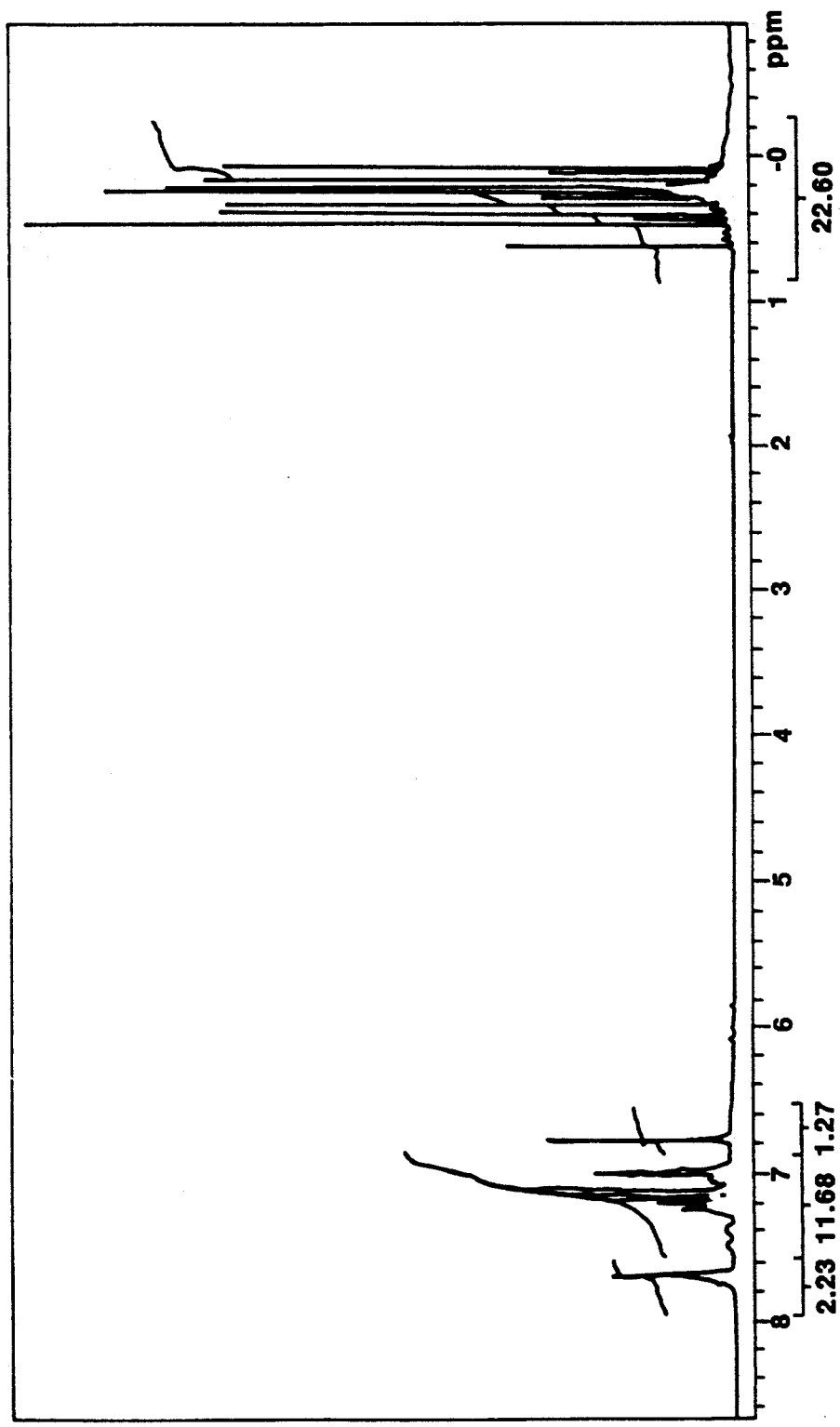
FIG. 5 is a NMR spectrum chart of the organic silicon compound of Reference Example.
Figure 6:
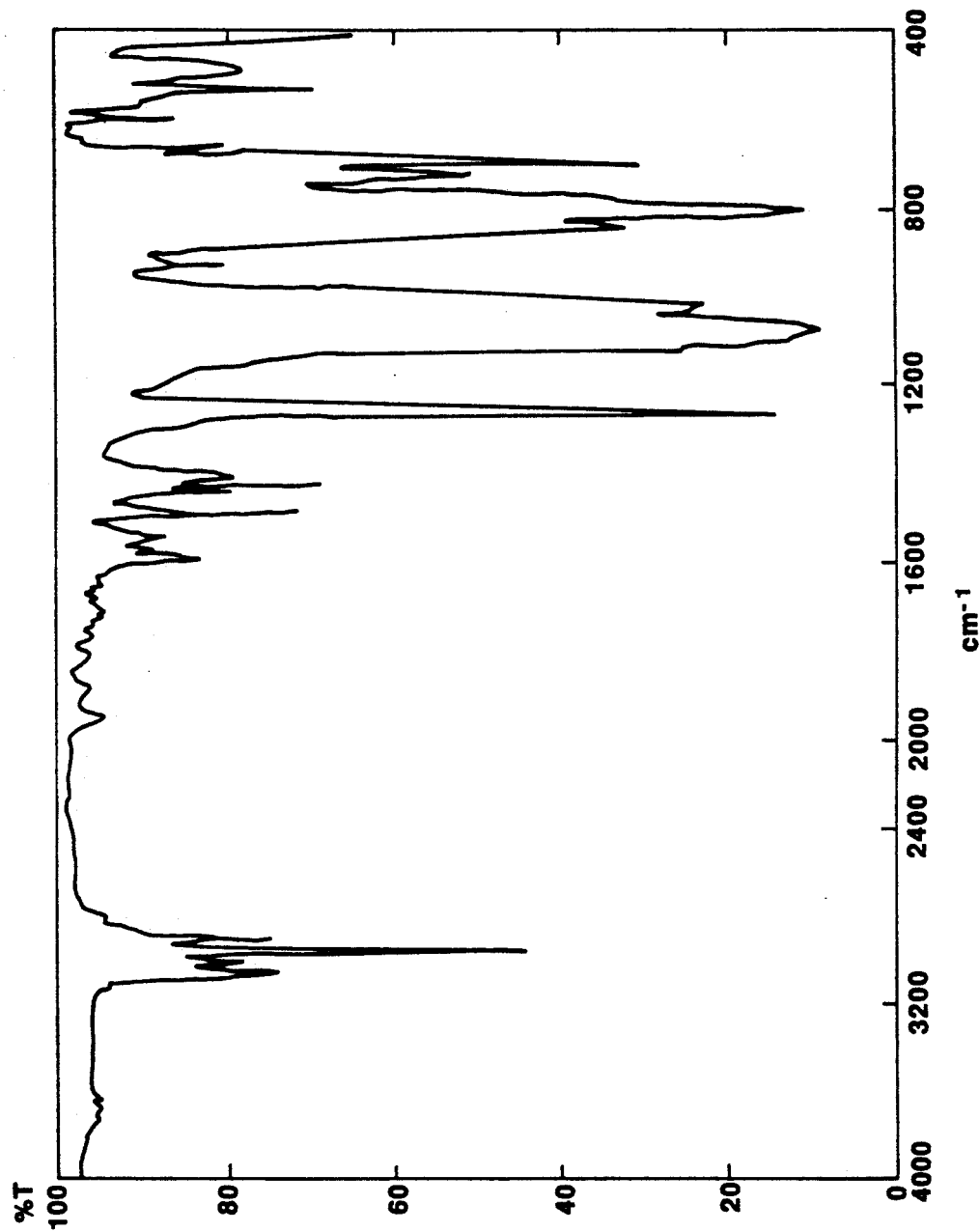
FIG. 6 is a IR spectrum chart of the organic silicon compound of Reference Example.

The reaction mixture was distilled under vacuum, obtaining two compounds having acetylene inserted in a Si—Si bond as seen from the following reaction scheme in a total weight of 0.30 g (0.68 mmol). The yield was 68%. FIGS. 5 and 6 show the NMR and IR spectra of this product, respectively.

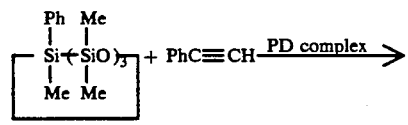

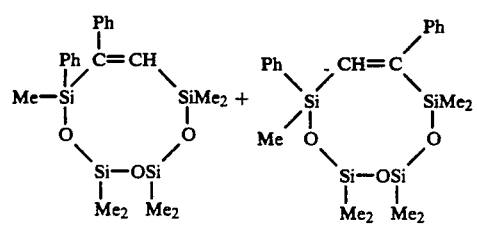

According to the method of the invention, novel organic silicon compounds having an aryl group-bearing Si—Si bond possessing a substantial UV absorption band in the UV region can be synthesized in high yields and high purity. The organic silicon compounds are effective for introducing a controlled amount of Si—Si bond into various polymers as by copolymerizing them with other cyclic siloxanes.

Although some preferred embodiments have been described, many modifications and variations may be made thereto in the light of the above teachings. It is therefore to be understood that within the scope of the appended claims, the invention may be practiced otherwise than as specifically described.

We claim:

1. An organic silicon compound of the general formula:

wherein Ar is a substituted or unsubstituted aryl group having 6 to 14 carbon atoms, $R^1$, $R^2$ and $R^3$ are independently monovalent hydrocarbon groups having 1 to 6 carbon atoms.

2. A method for preparing an organic silicon compound of the general formula:

wherein Ar is a substituted or unsubstituted aryl group having 6 to 14 carbon atoms, $R^1$, $R^2$ and $R^3$ are independently monovalent hydrocarbon groups having 1 to 6 carbon atoms, said method comprising reaction an α,ω-dichlorosiloxane of the general formula:

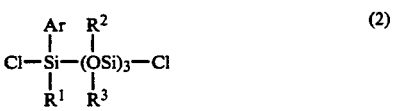

wherein Ar, $R^1$, $R^2$ and $R^3$ are as defined above with an alkali metal.

3. A method according to claim 2 wherein said α,ω-dichlorosiloxane of formula (2) is obtained by reacting a dichlorosilane of the general formula:

with a cyclotrisiloxane of the general formula:

in an aprotic polar solvent.

* * * * *